United States Patent
Capote et al.

(10) Patent No.: US 10,799,226 B2
(45) Date of Patent: Oct. 13, 2020

(54) SURGICAL ADAPTOR AND METHOD

(71) Applicant: Warsaw Orthopedic, Inc., Warsaw, IN (US)

(72) Inventors: Cristian A. Capote, Memphis, TN (US); Christopher T. Martin, Empire, MI (US); Steven Nowak, Traverse City, MI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1072 days.

(21) Appl. No.: 14/800,356

(22) Filed: Jul. 15, 2015

(65) Prior Publication Data

US 2017/0014119 A1 Jan. 19, 2017

(51) Int. Cl.
*A61B 17/02* (2006.01)
*A61B 90/50* (2016.01)
*A61B 90/57* (2016.01)

(52) U.S. Cl.
CPC .......... *A61B 17/0206* (2013.01); *A61B 90/50* (2016.02); *A61B 90/57* (2016.02)

(58) Field of Classification Search
CPC .............. A61B 17/0206; A61B 17/025; A61B 17/0293; A61B 90/50; A61B 2090/506; A61B 2090/508; A61B 2090/57; A61B 2090/571
USPC ........ 600/214, 215, 222, 227, 228–231, 234
See application file for complete search history.

(56) References Cited

U.S. PATENT DOCUMENTS

| | | | |
|---|---|---|---|
| 2,693,795 A | 11/1954 | Greishaber | |
| 3,626,471 A | 12/1971 | Florin | |
| 3,965,890 A | 6/1976 | Gauthier | |
| 4,718,151 A * | 1/1988 | LeVahn | |
| 4,971,038 A * | 11/1990 | Farley | A61B 17/02 24/525 |
| 5,027,793 A | 7/1991 | Engelhardt et al. | |
| 5,441,042 A | 8/1995 | Putman | |
| 5,727,899 A * | 3/1998 | Dobrovolny | A61B 17/02 403/384 |
| 5,891,144 A * | 4/1999 | Mata | A61B 17/6466 606/54 |
| 6,074,343 A | 6/2000 | Nathanson et al. | |
| 6,206,826 B1 | 3/2001 | Matthews et al. | |
| 6,322,500 B1 | 11/2001 | Sikra et al. | |
| 6,416,469 B1 | 7/2002 | Phung et al. | |

(Continued)

FOREIGN PATENT DOCUMENTS

| | | |
|---|---|---|
| WO | WO 2013/044151 A1 | 3/2013 |
| WO | 2015054070 A1 | 4/2015 |

OTHER PUBLICATIONS

European Search Report for EP 16825030.6 dated Feb. 11, 2019 (10 pages).

(Continued)

*Primary Examiner* — Anu Ramana
(74) *Attorney, Agent, or Firm* — Sorell, Lenna & Schmidt, LLP

(57) ABSTRACT

A surgical adaptor comprises a first member is attachable to a first surgical instrument having a projection that defines an axis. A second member is attachable to a second surgical instrument such that the second surgical instrument is movable in at least two degrees of freedom relative to the axis. Surgical systems, instruments and methods are disclosed.

20 Claims, 9 Drawing Sheets

(56) References Cited

U.S. PATENT DOCUMENTS

| | | | |
|---|---|---|---|
| 6,599,240 B2 | 7/2003 | Puchovsky et al. | |
| 6,808,493 B1 | 10/2004 | Bookwalter et al. | |
| 7,097,616 B2 * | 8/2006 | Bjork | A61B 1/32 600/230 |
| 7,122,036 B2 | 10/2006 | Vanacker | |
| 7,125,380 B2 * | 10/2006 | Yager | A61B 17/02 403/391 |
| 7,207,949 B2 | 4/2007 | Miles et al. | |
| 7,261,715 B2 * | 8/2007 | Rezach | A61B 17/7037 606/60 |
| 7,537,565 B2 | 5/2009 | Bass | |
| 7,582,058 B1 | 9/2009 | Miles et al. | |
| 7,691,057 B2 | 4/2010 | Miles et al. | |
| 7,785,253 B1 | 8/2010 | Arambula et al. | |
| 7,833,248 B2 * | 11/2010 | Markworth | A61B 17/7049 403/64 |
| 7,892,173 B2 | 2/2011 | Miles et al. | |
| 7,905,840 B2 | 3/2011 | Pimenta et al. | |
| 7,920,922 B2 | 4/2011 | Gharib et al. | |
| 7,935,051 B2 | 5/2011 | Miles et al. | |
| 7,959,653 B2 | 6/2011 | Thramann et al. | |
| 7,962,191 B2 | 6/2011 | Marino et al. | |
| 8,000,782 B2 | 8/2011 | Gharib et al. | |
| 8,005,535 B2 | 8/2011 | Gharib et al. | |
| 8,016,767 B2 | 9/2011 | Miles et al. | |
| 8,038,611 B2 | 10/2011 | Raymond et al. | |
| 8,055,349 B2 | 11/2011 | Gharib et al. | |
| 8,062,218 B2 | 11/2011 | Sebastian et al. | |
| D652,519 S | 1/2012 | Miles et al. | |
| D652,921 S | 1/2012 | Miles et al. | |
| D652,922 S | 1/2012 | Miles et al. | |
| 8,114,019 B2 | 2/2012 | Miles et al. | |
| 8,133,173 B2 | 3/2012 | Miles et al. | |
| 8,137,284 B2 | 3/2012 | Miles et al. | |
| 8,165,653 B2 | 4/2012 | Marino et al. | |
| 8,172,750 B2 | 5/2012 | Miles et al. | |
| 8,182,423 B2 | 5/2012 | Miles et al. | |
| 8,187,179 B2 | 5/2012 | Miles et al. | |
| 8,192,356 B2 | 6/2012 | Miles et al. | |
| 8,192,357 B2 | 6/2012 | Miles et al. | |
| D666,292 S | 8/2012 | Miles et al. | |
| D666,294 S | 8/2012 | Miles et al. | |
| 8,244,343 B2 | 8/2012 | Gharib et al. | |
| D666,923 S | 9/2012 | Buffington et al. | |
| 8,303,498 B2 | 11/2012 | Miles et al. | |
| 8,343,046 B2 | 1/2013 | Miles et al. | |
| 8,353,826 B2 | 1/2013 | Weiman | |
| 8,357,184 B2 | 1/2013 | Woolley et al. | |
| 8,535,320 B2 | 9/2013 | Woolley et al. | |
| 8,636,655 B1 | 1/2014 | Childs | |
| 8,657,819 B2 * | 2/2014 | Murner | |
| 8,882,662 B2 | 11/2014 | Charles | |
| 9,044,280 B1 | 6/2015 | Arambula et al. | |
| 2006/0224044 A1 | 10/2006 | Marchek et al. | |
| 2007/0208227 A1 | 9/2007 | Smith et al. | |
| 2008/0121765 A1 | 5/2008 | Fetzer | |
| 2011/0046448 A1 | 2/2011 | Paolitto et al. | |
| 2012/0245431 A1 | 9/2012 | Baudouin et al. | |
| 2012/0283521 A1 | 11/2012 | Smith et al. | |
| 2012/0296335 A1 | 11/2012 | Mullaney | |
| 2013/0096387 A1 | 4/2013 | Deridder et al. | |
| 2013/0190575 A1 | 7/2013 | Mast et al. | |
| 2013/0211457 A1 | 8/2013 | Dickinson et al. | |
| 2014/0135584 A1 | 5/2014 | Lee et al. | |
| 2015/0088030 A1 | 3/2015 | Taylor | |
| 2015/0100129 A1 | 4/2015 | Waugh et al. | |

OTHER PUBLICATIONS

International Search Report for PCT/US2016/041879 dated Oct. 12, 2016 (2 pages).

Australian Government IP Australia, Examination report No. 1 for standard patent application, Application No. 2016291735, Applicant name Warsaw Orthopedic, Inc., dated Apr. 14, 2020.

\* cited by examiner

SURGICAL ADAPTOR AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy, corpectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior technologies.

SUMMARY

In some embodiments, a surgical adaptor is provided. The surgical adaptor includes a first member attachable to a first surgical instrument having a projection that defines an axis. A second member is attachable to a second surgical instrument such that the second surgical instrument is movable in at least two degrees of freedom relative to the axis. In some embodiments, surgical systems, instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
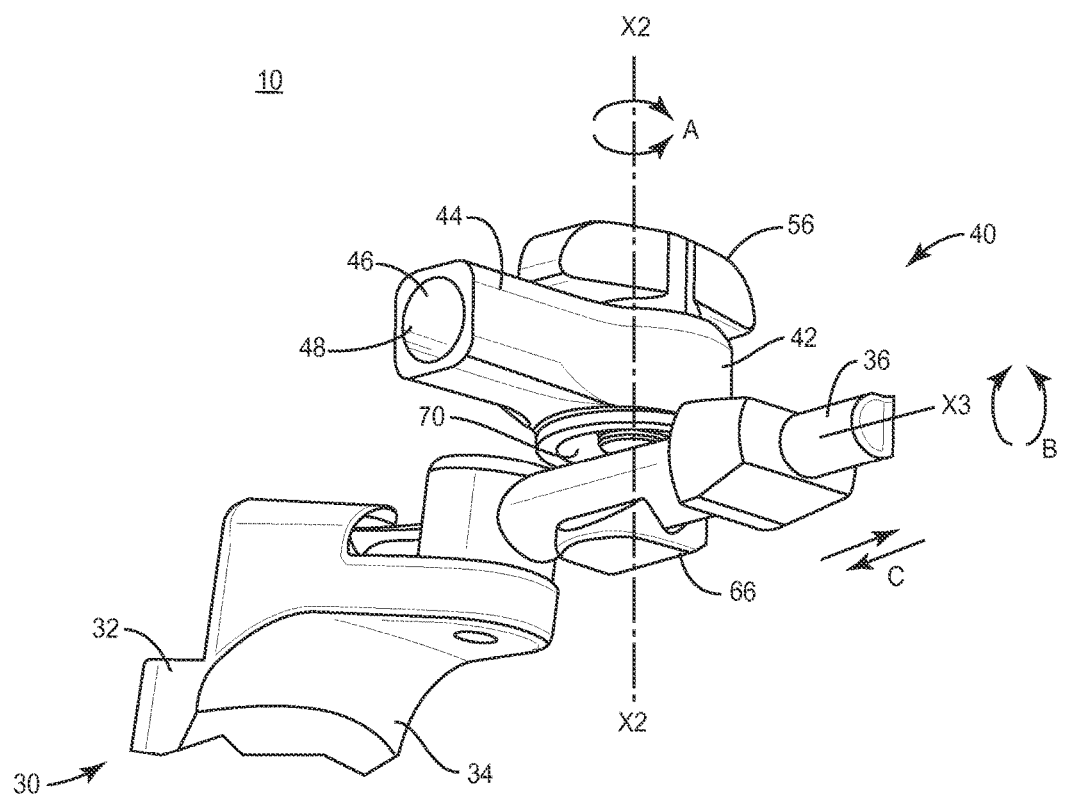
FIG. 1 is a break away perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which employ a selected surgical pathway. In some embodiments, the surgical systems and methods of the present disclosure are employed with a spinal joint fusion, for example, with a cervical, thoracic, lumbar and/or sacral region of a spine. In some embodiments, the present system includes a surgical instrument, such as, for example, an adaptor that connects a first surgical instrument and a second surgical instrument.

In some embodiments, the surgical system comprises an adaptor that connects with a surgical instrument, such as, for example, a retractor having a longitudinal element fixed therewith that is movable in a plurality of degrees of freedom relative to the retractor. In some embodiments, the longitudinal element is capable of movement in at least two degrees of freedom. In some embodiments, the longitudinal element is capable of movement in at least three degrees of freedom. In some embodiments, the adaptor comprises an instrument connection and a release mechanism.

In some embodiments, the surgical system comprises an adaptor configured as a surgical instrument connection and release mechanism. In some embodiments, the surgical system is employed with a method of attaching and disconnecting surgical instruments. In some embodiments, the surgical system comprises an adaptor configured as a surgical instrument connection and release mechanism for a retractor with retractor blades and/or a retractor rack. In some embodiments, the adaptor is employed with a method of attaching and disconnecting the retractor with retractor blades and/or a retractor rack.

In some embodiments, the surgical system is configured to provide relative movement in multiple degrees of freedom and can be secured firmly using hand force only. In some embodiments, the surgical system is configured to achieve high holding strength with hand force alone. In some embodiments, the surgical system comprises a plurality of fixation arms configured to secure several retractor blades. In some embodiments, an adaptor is provided to facilitate connection between each of a plurality of fixation arms and several retractor blades.

In some embodiments, the surgical system comprises a retractor system having a connection, such as, for example, an adaptor disposed between at least one fixation arm and at least one retractor blade that provides relative movement in three degrees of freedom. In some embodiments, the adaptor includes two degrees of freedom in rotation and one degree of freedom for translation. In some embodiments, the fixation arm comprises a jaw and a collar assembly that is drawn together using a threaded knob. In some embodiments, the assembly comprises a spring and is spring loaded in a closed position or an up position to provisionally retain a shaft connected with the blade before it is locked. In some embodiments, the assembly can be locked at a selected angle relative to the fixation arm. In some embodiments, the fixation arm comprises a collar component and a jaw component. In some embodiments, the assembly comprises a spring in a selected location and the spring preloads the assembly. In some embodiments, the assembly is preloaded in an upward direction. In some embodiments, the jaw component includes a lead in edge that allows a snap on provisional connection.

In some embodiments, the surgical system comprises an adaptor having splines on a shaft and collar components comprising splines. In some embodiments, the adaptor has a splined geometry that creates a gear interface between the shaft and the collar, allowing them to lock together at angular increments. In some embodiments, this configuration results in a connection with high shear strength while requiring a low torque input from threads. In some embodiments, hand tightening only is sufficient to achieve a high amount of connection strength. In some embodiments, this configuration allows movement including three degrees of freedom.

In some embodiments, the adaptor comprises a smooth central portion, such as, for example, having no splines to facilitate locating a connector on the shaft and reduces manufacturing complexity for a jaw component. In some embodiments, the configuration comprises movement having two degrees of freedom in rotation and is not configured for translation.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
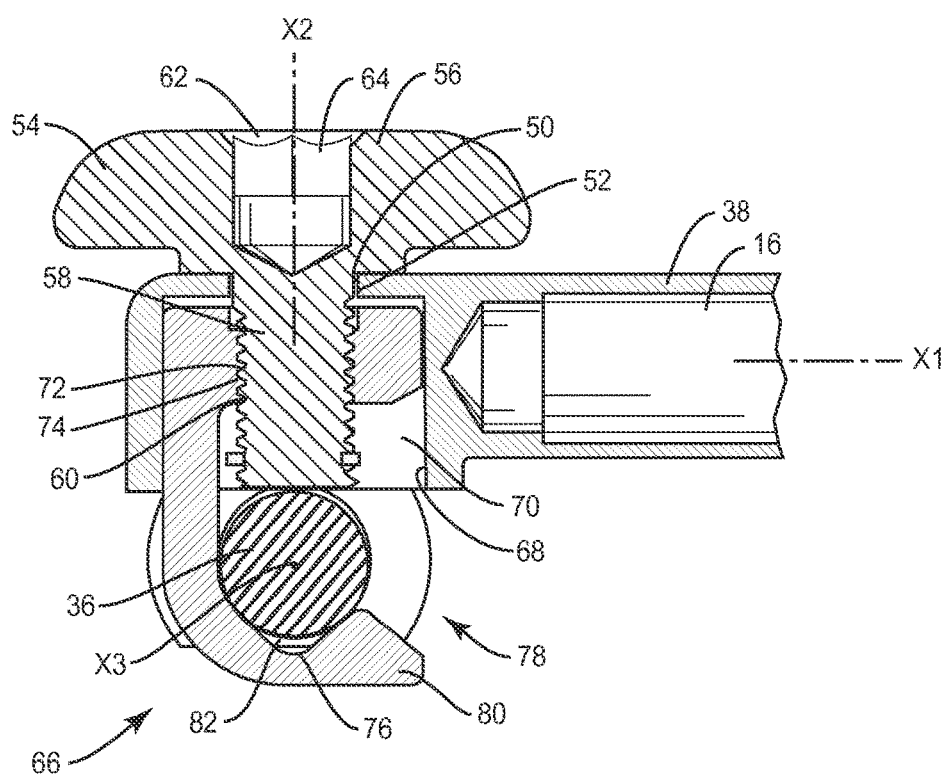
FIG. 2 is a cross section view of the components shown in FIG. 1.
Figure 3:
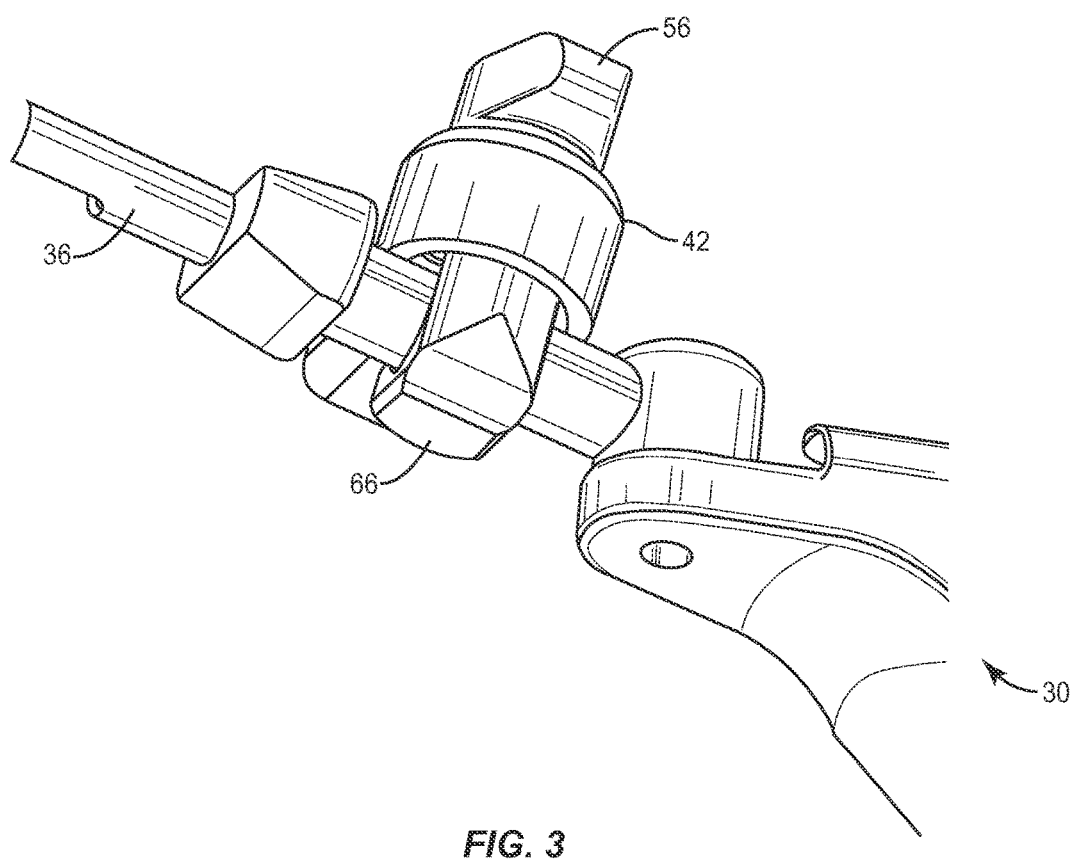
FIG. 3 is a break away view of the components shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL®)), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TOP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Figure 4:
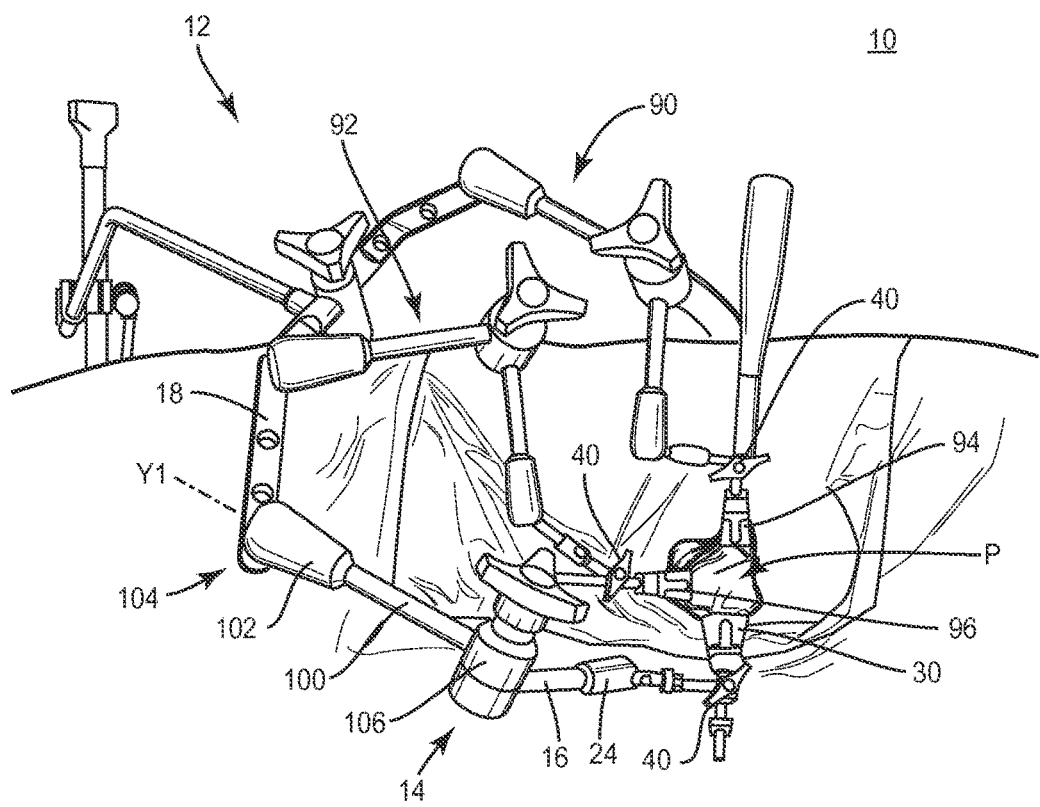
FIG. 4 is a perspective view of components of one embodiment of a system in accordance with the principles of the present disclosure disposed with a patient body.

Surgical system 10 includes a surgical instrument, such as, for example, a surgical retractor 12, as shown in FIG. 4, including a retractor arm 14. In some embodiments, retractor arm 14 includes a projection, such as, for example, an extension 16. Extension 16 defines an axis X1. In some embodiments, retractor arm 14 is attached with a rail 18 such that arm 14 is movable in one or a plurality of degrees of freedom to one or a plurality of orientations relative to rail 18, stationary surgical equipment and/or a subject body B in connection with a surgical procedure. In some embodiments, the degrees of freedom of movement of arm 14 to one or a plurality of orientations relative to rail 18, stationary surgical equipment and/or subject body B can include one or a plurality of degrees of movement in translation, one or a plurality of degrees of movement in rotation, planar movement such as a four bar linkage, spherical movement such as poly-axial and/or joints or links such as a kinematic chain. In some embodiments, the degrees of movement in translation can include up, down, left, right, forward and/or backward. In some embodiments, the degrees of movement in rotation can include tilting, swiveling and/or pivoting in one or a plurality directions. In some embodiments, retractor arm 14 is independently and selectively movable relative to rail 18, stationary surgical equipment and/or subject body B. In some embodiments, extension 16 includes a tubular collar 20 that defines a socket 22. Socket 22 forms a spheroidal joint, such as, for example, a ball joint 24.

Figure 5:
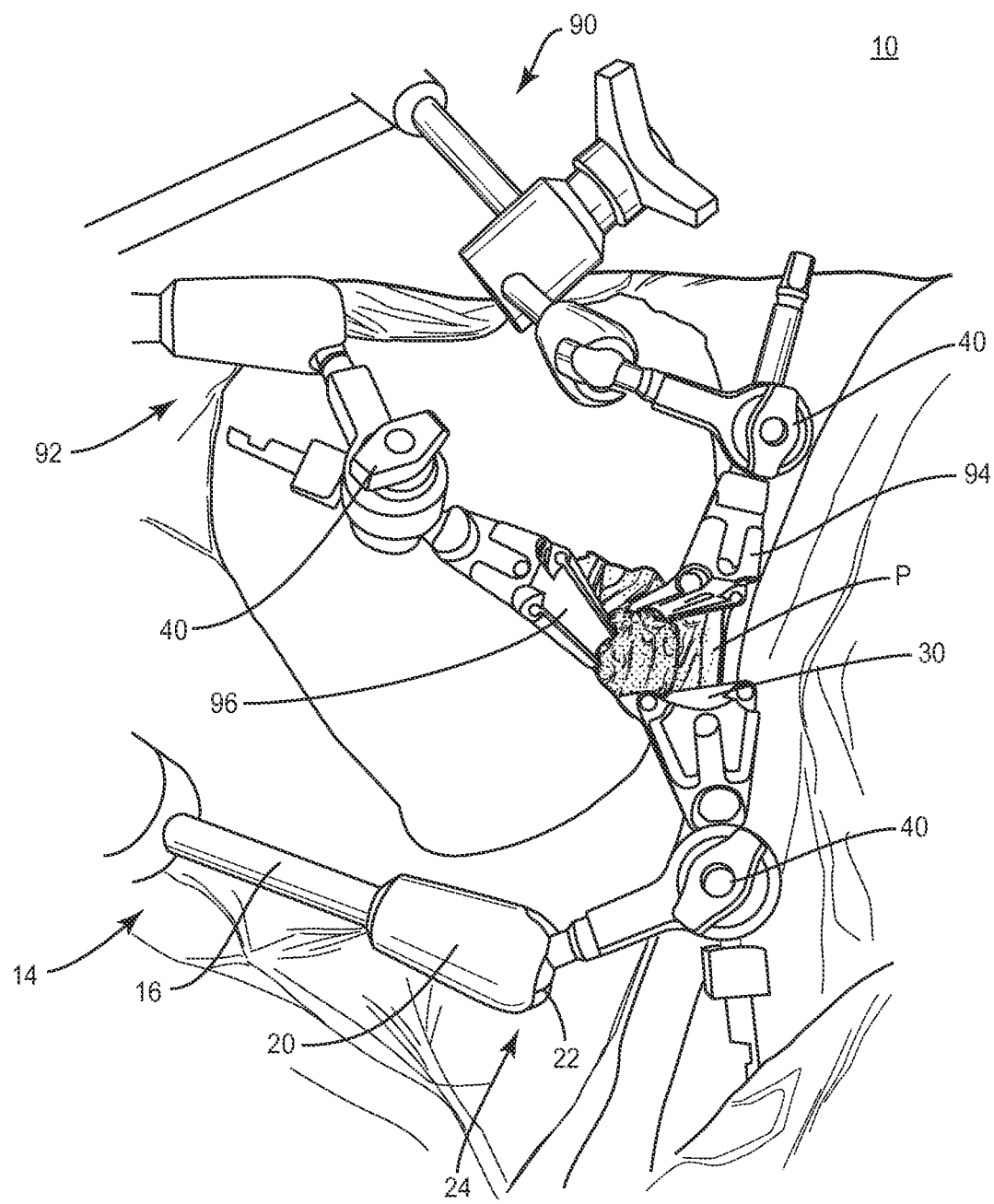
FIG. 5 is a perspective view of components of one embodiment of a system in accordance with the principles of the present disclosure disposed with a patient body.

In some embodiments, the configuration of surgical retractor 12 provides retractor arm 14 connected to a surgical instrument, such as, for example, a retractor blade 30. Retractor blade 30 includes an outer surface 32 configured for engaging and spacing apart tissue. Retractor blade 30 includes an inner surface 34 configured to define a portion of a surgical pathway P (FIG. 5). Retractor blade 30 includes arm 36, as shown in FIG. 1, configured for connection with retractor arm 14, extension 16 and/or an adaptor 40, as described herein. In some embodiments, all or only a portion of blade 30 may have various cross-section configurations, such as, for example, arcuate, cylindrical, oblong, rectangular, polygonal, undulating, irregular, uniform, non-uniform, consistent, variable, and/or U-shape. In some embodiments, surface 32 and/or surface 34 may have alternate surface configurations, such as, for example, rough, undulating, porous, semi-porous, dimpled, polished and/or textured.

Adaptor 40 is configured to connect surgical retractor 12 with retractor blade 30 for relative movement therebetween. Adaptor 40 attaches surgical retractor 12 with retractor blade 30 such that retractor blade 30 is movable in a plurality of degrees of freedom to one or a plurality of orientations, relative to axis X1 and/or extension 16, stationary surgical equipment and/or subject body B in connection with a surgical procedure, as described herein. In some embodiments, adaptor 40 is independently and selectively moveable relative to axis X1 and/or extension 16 to facilitate positioning of adaptor 40 and/or blade 30, as described herein.

Adaptor 40 includes a member, such as, for example, a collar 42. Collar 42 includes an extension 44 having a surface 46. Surface 46 defines an opening 48 configured for disposal of extension 16. In some embodiments, surface 46 and a surface of extension 16 comprise a spheroidal joint, similar to ball joint 24, to facilitate relative movement of adaptor 40 and extension 16. In some embodiments, surface 46 may have alternate surface configurations, such as, for example, rough, undulating, porous, semi-porous, dimpled, polished and/or textured.

Collar 42 includes a surface 50 that defines an opening 52. Opening 52 is configured for disposal of an actuator, such as, for example, a handle 54. Handle 54 includes a knob 56 and a shaft 58. Knob 56 includes a surface 62 that defines a socket 64. In some embodiments, socket 64 includes a hexalobe geometry configured for disposal of a similarly shaped bit of a tool, such as, for example, a driver (not shown) to engage knob 56 to rotate shaft 58, as described herein. In some embodiments, socket 64 has a cruciform, phillips, square, hexagonal, polygonal, star cross sectional configuration configured for disposal of a correspondingly shaped portion of a driver.

Shaft 58 includes a threaded surface 60 disposed in a threaded engagement with a member, such as, for example, a jaw 66 such that jaw 66 is translatable relative to shaft 58. In some embodiments, threaded surface 60 may include a single thread turn or a plurality of discrete threads. In some embodiments, other engaging structures may be located on shaft 58, such as, for example, nail configuration, barbs, expanding elements, raised elements and/or spikes.

Collar 42 includes an inner surface 68 that defines a cavity 70 configured for disposal of jaw 66, as described herein. In some embodiments, cavity 70 includes a rectangular configuration. In some embodiments, all or only a portion of cavity 70 may have a varied cross-section configuration, such as, for example, arcuate, cylindrical, oblong, polygonal, undulating, irregular, uniform, non-uniform, consistent, variable, and/or U-shape. In some embodiments, surface 68 may have alternate surface configurations, such as, for example, rough, undulating, porous, semi-porous, dimpled, polished and/or textured.

Jaw 66 includes an inner surface 72 that defines a threaded passageway 74. Passageway 74 is configured for disposal and threaded fixation with shaft 58. Jaw 66 is engageable with handle 54 in threaded fixation to dispose blade 30 with retractor arm 14 between a non-locked position and a locked position. Shaft 58 is engaged with jaw 66 to define an axis X2.

Jaw 66 includes a surface 76 that defines a cavity, such as, for example, a lateral passageway 78. Passageway 78 is configured for disposal of arm 36, which defines an axis X3. Surface 76 includes a retaining flange 80. Flange 80 defines a recess 82 with surface 76 configured for disposal of arm 36. In some embodiments, flange 80 is oriented in a snap fit configuration to retain arm 36 with adaptor 40. In some embodiments, adaptor 40 includes a spring (not shown) disposed within cavity 70 to bias adaptor 40 in a provisionally closed or locked position with arm 36 to retain arm 36 with adaptor 40 prior to fixation of retractor arm 14 in a final locked orientation. In some embodiments, the provisionally closed or locked position includes jaw 66 being biased and/or drawn upwardly with arm 36 relative to cavity 70. In some embodiments, the spring (not shown) is disposed about shaft 58. In some embodiments, the spring (not shown) is disposed between jaw 66 and surface 68.

Adaptor 40 is fixed with extension 16. Arm 36 is disposed with passageway 78. In some embodiments, adaptor 40 connects retractor arm 14 with retractor blade 30 such that retractor blade 30 is movable to a plurality of degrees of freedom. In some embodiments, adaptor 40 is spring preloaded to bias handle 54 and/or jaw 66 to a provisionally closed or locked configuration with arm 36 to retain arm 36 with adaptor 40 prior to fixation of retractor arm 14 in a final locked configuration. In some embodiments, adaptor 40 connects retractor arm 14 with retractor blade 30 to dispose retractor arm 14 and retractor blade 30 in a non-locked configuration, a provisionally locked configuration and/or a final locked configuration, as described herein.

Adaptor 40 is configured for attaching retractor arm 14 with retractor blade 30. Adaptor 40 connects retractor arm 14 with retractor blade 30 and facilitates relative movement of arm 36 and extension 16. In some embodiments, adaptor 40 connects retractor arm 14 with retractor blade 30 such that retractor blade 30 is movable in one or a plurality of degrees of freedom, as described herein, to one or a plurality of orientations relative to rail 18, stationary surgical equipment and/or subject body B in connection with a surgical procedure. In some embodiments, adaptor 40 connects retractor arm 14 with retractor blade 30 such that retractor blade 30 is movable in a plurality of degrees of freedom including two degrees of freedom in rotation and one degree of freedom in translation, relative to extension 16. In some embodiments, adaptor 40 connects retractor arm 14 with retractor blade 30 such that retractor blade 30 is independently and selectively moveable relative to retractor arm 14 to facilitate positioning of retractor blade 30, as described herein.

In some embodiments, retractor blade 30 is disposed in a non-locked configuration and movable in at least three additional degrees of freedom as facilitated by adaptor 40 including two degrees of freedom in rotation and one degree of freedom in translation, relative to extension 16. Arm 36 is rotatable relative to and about axis X2, in the direction shown by arrows A in FIG. 1, rotatable relative to and about axis X3, in the direction shown by arrows B in FIG. 1, and translatable relative to and along axis X3, in the direction shown by arrows C in FIG. 1, to one or more selected orientations relative to extension 16. In some embodiments, retractor blade 30 is disposed in a provisionally locked configuration and movable, as described herein, for selective and/or incremental adjustment of position and orientation of retractor blade 30 relative to retractor arm 14. Upon positioning of retractor blade 30 relative to extension 16 in a selected orientation, as described herein, a driver is engaged with socket 64 and/or handle 54 is manipulated to rotate shaft 58 in threaded engagement with jaw 66. Shaft 58 engages arm 36 to lock blade 30 in final locked configuration with extension 16.

Retractor arm 14 is connected with rail 18 at a projection disposed adjacent an end portion of rail 18. Retractor arm 14 includes extension 16, as described herein, and an extension 100. The projection defines an axis Y1. The projection includes a bearing, such as, for example, a ball (not shown) that is connected with extension 100. Arm 14 is movable in a plurality of degrees of freedom to one or a plurality of orientations, relative to rail 18, stationary surgical equipment and/or subject body B in connection with a surgical procedure. Extension 100 includes a tubular collar 102 that defines a socket configured for disposal of the ball (not shown) to form a spheroidal joint, such as, for example, a ball joint 104. Extension 100 is movable in a plurality of degrees of freedom to one or a plurality of orientations, such as, for example, poly-axial relative to rail 18, stationary surgical equipment and/or subject body B in connection with a surgical procedure. In some embodiments, ball joint 104 provides rotation of extension 100 relative to axis Y1 and disposal of extension 100 at a plurality of orientations relative to axis Y1. In some embodiments, extension 100 is movable relative to rail 18 between a first orientation and a second orientation in which extension 100 is moveable through an angular range relative to axis Y1. In some embodiments, the orientations relative to axis Y1 may include, such as, for example, transverse, perpendicular, angular orientations such as acute or obtuse, coaxial and/or may be offset or staggered.

Extension 100 is connected with extension 16 by a pivot joint 106 that is disposable between a movable orientation and a locked orientation. In some embodiments, pivot joint 106 includes disc shaped collars. In some embodiments, the disc shaped collars include splined surfaces for incremental and selective positioning. Pivot joint 106 is configured to facilitate rotation of extension 16 relative to extension 100 for positioning of blade 30 relative to rail 18, stationary surgical equipment and/or subject body B.

In some embodiments, retractor blade 30 is disposable in a configuration to space tissue of the incision to define a surgical pathway P relative to a bilateral axis of subject body B, as described herein. In some embodiments, retractor blade 30 is movable relative to extension 16 between a first orientation and a second orientation in which retractor blade 30 is moveable through an angular range relative to extension 16 via ball joint 24. In some embodiments, retractor blade 30 is configured to achieve a unique angle of trajectory and is unconstrained by placement of adjacent blades, as described herein.

In some embodiments, surgical retractor 12 includes one or a plurality of independent arms, such as, for example, retractor arm 14 and/or retractor arms 90 and 92, as shown in FIG. 4, which are similarly configured to retractor arm 14. In some embodiments, retractor arm 90 is connected to an adaptor 40, as described herein and similar to arm 14, for attaching retractor arm 90 with a retractor blade 94, similar to retractor blade 30 described herein. Adaptor 40 connects retractor arm 90 with retractor blade 94 and facilitates relative movement of blade 94 in one or a plurality of degrees of freedom to one or a plurality of orientations relative to arm 90. In some embodiments, retractor arm 92 is connected to an adaptor 40, as described herein and similar to arm 14, for attaching retractor arm 92 with a retractor blade 96, similar to retractor blade 30 described herein. Adaptor 40 connects retractor arm 92 with retractor blade 96 and facilitates relative movement of blade 96 in one or a plurality of degrees of freedom to one or a plurality of orientations relative to arm 92.

In some embodiments, adaptor 40 may be employed with alternately configured retractors, retractor arm and/or retractor blades. In some embodiments, adaptor 40 may be employed with various surgical instruments, similar to connection of adaptor 40 with retractor 12, retractor arm 14 and/or retractor blade 30, such as, for example, drivers, extenders, reducers, spreaders, distractors, clamps, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, surgical system 10, similar to the systems and methods described herein, is employed with a surgical procedure for treatment of a spinal disorder, such as those described herein, affecting a section of a spine of a patient. Surgical system 10 may also be employed with other surgical procedures. In some embodiments, surgical system 10 is employed to implant components, such as bone fasteners, rods, interbody devices and plates, with the body.

With the body disposed in a selected orientation, a medical practitioner makes and/or creates an incision in tissue, which includes soft tissue and/or muscle, to obtain access to a surgical site including affected vertebral levels. In some embodiments, the tissue comprises an anterior portion, a posterior portion, a caudal portion and/or a cephalad portion disposed adjacent to the incision. The tissue is manipulated to space the tissue adjacent to the incision. Manipulation of the tissue in the anterior, posterior, caudal and cephalad orientations creates a surgical pathway P to a surgical site including vertebrae.

A surgical instrument, such as, for example, surgical retractor 12, as described herein, is disposed with incision I and in communication with surgical pathway P for spacing tissue. Retractor blades 30, 94, 96, as described herein, are configured for insertion sequentially around the intervertebral space to protect tissue and/or vessels, as described herein. Rail 18 is attached to surgical equipment, as described herein. In some embodiments, an adaptor 40 is attached with arms 14, 90 and/or 92 and blades 30, 94 and/or 96, as shown in FIGS. 4 and 5, similar to that described herein.

Adaptor 40 connects arms 14, 90 and/or 92 with blades 30, 94 and/or 96, as described herein, such that one or more of the blades is movable in a plurality of degrees of freedom to one or a plurality of orientations, relative to rail 18, one or more of the retractor arms, stationary surgical equipment and/or tissue of subject body B adjacent the surgical site in connection with a surgical procedure.

In some embodiments, blade 30 is manipulated for movement, as described herein, via adaptor 40 and/or retractor arm 14 relative to incision I to align and guide blade 30 into an anterior orientation and/or engagement with an anterior portion of incision I relative to body B. In some embodiments, blade 94 is manipulated for movement, as described herein, via adaptor 40 and/or retractor arm 90 relative to incision I to align and guide blade 94 into a posterior orientation and/or engagement with a posterior portion of incision I relative to body B. In some embodiments, blade 96 is manipulated for movement, as described herein, via adaptor 40 and/or retractor arm 92 relative to incision I to align and guide blade 96 into a cephalad orientation and/or engagement with a cephalad portion of incision I relative to body B.

In some embodiments, a discectomy is performed via surgical pathway P. In some embodiments, instruments, such as, for example, a Cobb elevator, mallet, shaver, serrated curettes, rasp, a ring curette, a uterine curette and/or a combination thereof are utilized to perform a discectomy of the disc space.

In some embodiments, trial implants (not shown) are delivered along surgical pathway P. The trial implants are used to distract one or more intervertebral spaces of the vertebral levels and apply appropriate tension in the intervertebral space allowing for indirect decompression. In one embodiment, a direct decompression of the disc space is performed by removing a portion of a herniated disc. In some embodiments, one or a plurality of interbody implants can be introduced and delivered along surgical pathway P for implantation with one or more intervertebral spaces of the vertebral levels.

In some embodiments, pilot holes or the like are made in vertebrae adjacent the intervertebral space, via surgical pathway P for receiving bone fasteners and/or attaching spinal constructs, which may include rods and plates. An inserter is attached with the implants and/or spinal constructs for delivery along surgical pathway P adjacent to a surgical site for implantation adjacent one or more vertebra and/or intervertebral spaces of the vertebral levels.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft allograft, xenograft, autograft, bone paste, bone chips, Skelite®, and/or BMP to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration. In such embodiments, titanium coatings may be applied via a variety of methods, including but not limited to plasma spray coating and/or mechanical attachment of titanium plates to form a PEEK/Titanium implant.

Figure 6:
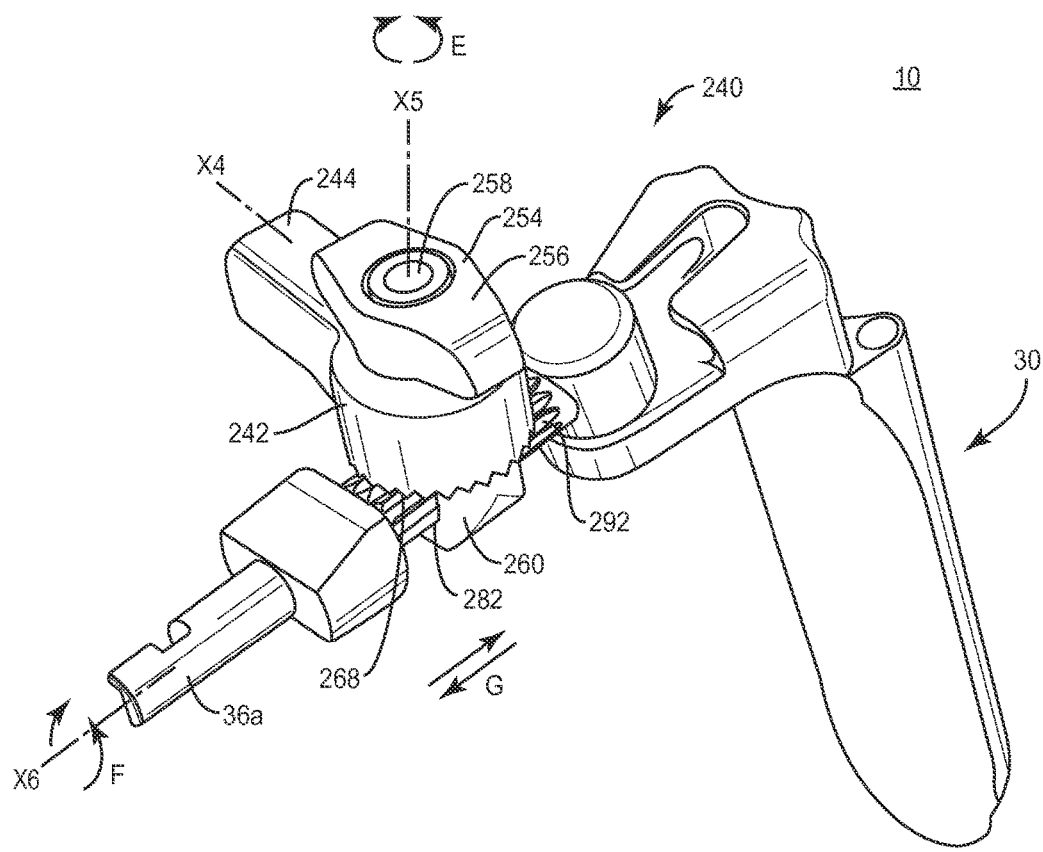
FIG. 6 is a break away perspective view of components of one embodiment of a surgical system in accordance with the principles of the present disclosure.
Figure 7:
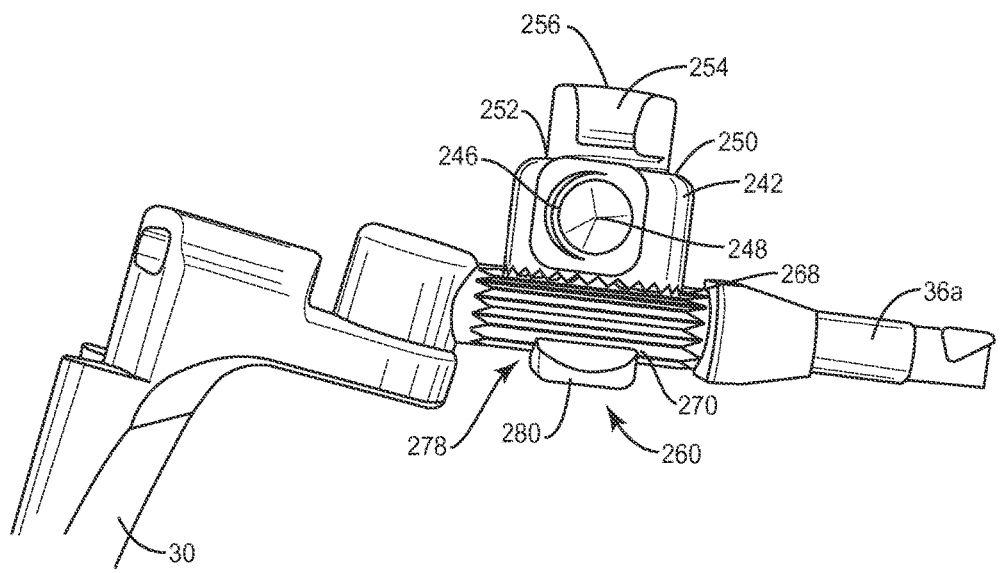
FIG. 7 is a side view of the components shown in FIG. 6.
Figure 8:
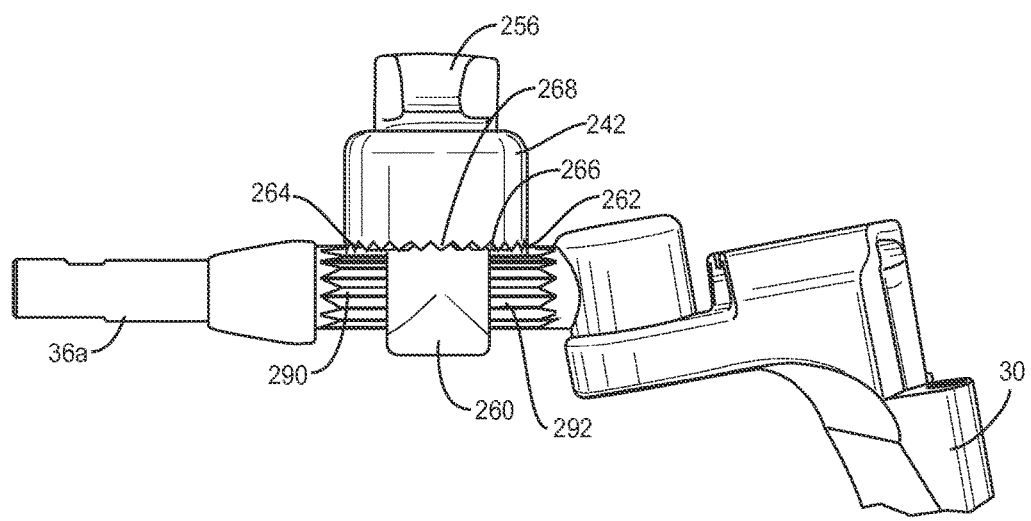
FIG. 8 is a side view of the components shown in FIG. 6.

In one embodiment, as shown in FIGS. 6-8, surgical system 10, similar to the systems and methods described herein, includes an adaptor 240, similar to adaptor 40 described herein, and comprises retractor 12 with retractor arm 14 including extension 16, and blade 30, as described herein.

Adaptor 240 is configured to connect surgical retractor 12 with retractor blade 30 for relative movement therebetween. Adaptor 240 attaches surgical retractor 12 with retractor blade 30 such that retractor blade 30 is movable in a plurality of degrees of freedom to one or a plurality of orientations, relative to axis X1 and/or extension 16, stationary surgical equipment and/or subject body B in connection with a surgical procedure, as described herein. In some embodiments, adaptor 240 is independently and selectively moveable relative to axis X1 and/or extension 16 to facilitate positioning of adaptor 240 and/or blade 30, as described herein.

Adaptor 240 includes a collar 242. Collar 242 includes an extension 244 having a surface 246. Surface 246 defines an opening 248 configured for disposal of extension 16. Extension 244 defines an axis X4. In some embodiments, surface 246 and a surface of extension 16 comprise a spheroidal joint, similar to that described herein to facilitate relative movement of adaptor 240 and extension 16. Collar 242 includes a surface 250 that defines an opening 252. Opening 252 is configured for disposal of a handle 254. Handle 254 includes a knob 256 and a shaft (not shown), similar to shaft 58. Knob 256 includes a surface that defines a socket 258. In some embodiments, socket 258 includes a hexalobe geometry configured for disposal of a similarly shaped bit of a tool, such as, for example, a driver (not shown) to engage knob 256 to rotate the shaft, as described herein. The shaft includes a threaded surface (not shown) disposed in a threaded engagement with a member, such as, for example, a jaw 260, similar to jaw 66, such that jaw 260 is translatable relative to the shaft.

Collar 242 includes an inner surface 262 that defines a cavity 264 configured for disposal of jaw 260, as described herein. Collar 242 includes a surface 266 that includes a radially splined surface 268. Surface 268 is configured to engage a longitudinal or axial splined surface of arm 36*a* to facilitate incremental and selective positioning of blade 30.

Jaw 260 includes an inner surface that defines a threaded passageway (not shown). The passageway is configured for disposal and threaded fixation with the shaft. In some embodiments, jaw 260 is engageable with handle 254 in threaded fixation to dispose blade 30 with retractor arm 14 between a non-locked configuration, a provisionally locked configuration and a final locked configuration, similar to that described herein. The shaft is engaged with jaw 260 to define an axis X5.

Jaw 260 includes a surface 276 that defines a cavity, such as, for example, a lateral passageway 278. Passageway 278 is configured for disposal of arm 36*a*, which defines an axis X6. Surface 276 includes a retaining flange 280. Flange 280 defines a recess 282 with surface 276 configured for disposal of arm 36*a*. In some embodiments, flange 280 is oriented in a snap fit configuration to retain arm 36*a* with adaptor 240. In some embodiments, adaptor 240 includes a spring (not shown) disposed within cavity 264 to bias adaptor 240 in a provisionally closed or locked configuration with arm 36*a* to retain arm 36*a* with adaptor 240 prior to fixation of retractor arm 14 in a final orientation. In some embodiments, the provisionally closed or locked configuration includes jaw 260 being biased and/or drawn upwardly with arm 36*a* relative to cavity 264. In some embodiments, the spring (not shown) is disposed about the shaft. In some embodiments, the spring (not shown) is disposed between jaw 260 and surface 262.

Arm 36*a* includes a surface 290 including longitudinal or axial splines 292. Splines 292 are configured for engagement with surface 268 to facilitate incremental and selective positioning of blade 30 relative to arm 14. Surface 268 and splines 292 form a gear interface between collar 242 and arm 36*a*. In some embodiments, the gear interface facilitates locking of arm 36*a* with adaptor 240 at angular increments providing for a higher shear strength requiring a low torque input from the threaded engagement with the shaft and jaw 260. In some embodiments, the low torque allows for a practitioner to hand tighten adaptor 240.

Adaptor 240 is fixed with extension 16. Arm 36*a* is disposed with passageway 278. In some embodiments, adaptor 240 connects retractor arm 14 with retractor blade 30 such that retractor blade 30 is movable to a plurality of degrees of freedom. In some embodiments, adaptor 240 is spring pre-loaded to bias handle 254 and/or jaw 260 to a provisionally closed or locked configuration with arm 36*a* to retain arm 36*a* with adaptor 240 prior to fixation of retractor arm 14 in a final locked configuration. In some embodiments, adaptor 240 connects retractor arm 14 with retractor blade 30 to dispose retractor arm 14 and retractor blade 30 in a non-locked configuration, a provisionally locked configuration and/or a final locked configuration, as described herein.

Adaptor 240 is configured for attaching retractor arm 14 with retractor blade 30. Adaptor 240 connects retractor arm 14 with retractor blade 30 and facilitates relative movement of arm 36*a* and extension 16. In some embodiments, adaptor 240 connects retractor arm 14 with retractor blade 30 such that retractor blade 30 is movable in one or a plurality of degrees of freedom, as described herein, to one or a plurality of orientations relative to rail 18, stationary surgical equipment and/or subject body B in connection with a surgical procedure. In some embodiments, adaptor 240 connects retractor arm 14 with retractor blade 30 such that retractor blade 30 is movable in a plurality of degrees of freedom including two degrees of freedom in rotation and one degree of freedom in translation, relative to extension 16. In some embodiments, adaptor 240 connects retractor arm 14 with retractor blade 30 such that retractor blade 30 is independently and selectively moveable relative to retractor arm 14 to facilitate positioning of retractor blade 30, as described herein.

In some embodiments, retractor blade 30 is disposed in a non-locked configuration and movable in three additional degrees of freedom as facilitated by adaptor 240 including two degrees of freedom in rotation and one degree of freedom in translation, relative to extension 16. Arm 36*a* is rotatable relative to and about axis X5, in the direction shown by arrows E in FIG. 6, rotatable relative to and about axis X6, in the direction shown by arrows F in FIG. 6, and translatable relative to and along axis X6, in the direction shown by arrows G in FIG. 6, to one or more selected orientations relative to extension 16. In some embodiments, retractor blade 30 is disposed in a provisionally locked configuration and movable, as described herein, for selective and/or incremental adjustment of position and orientation of retractor blade 30 relative to retractor arm 14. Upon positioning of retractor blade 30 relative to extension 16 in a selected orientation, as described herein, a driver is engaged with socket 258 and/or handle 254 is manipulated to rotate the shaft in threaded engagement with jaw 260. The shaft engages arm 36*a* to lock blade 30 in final locked configuration with extension 16.

Figure 9:
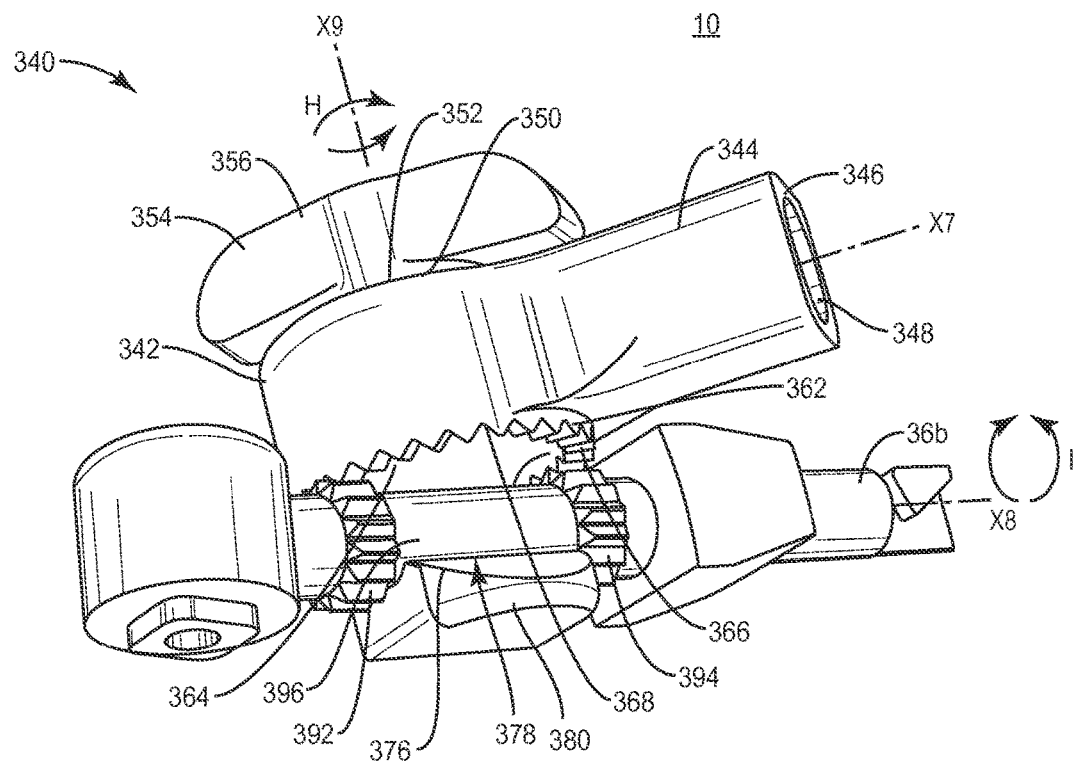
FIG. 9 is a break away perspective view of components of one embodiment of a surgical system in accordance with the principles of the present disclosure.
Figure 10:
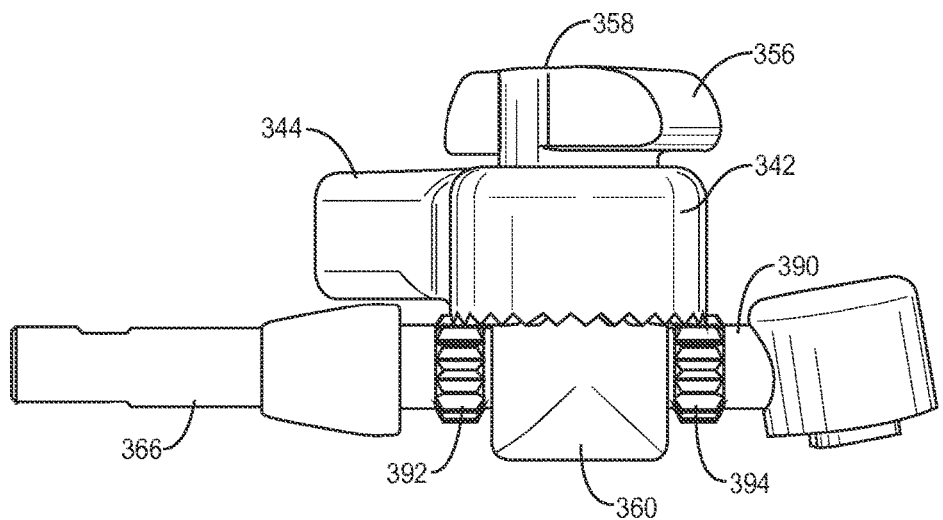
FIG. 10 is a side view of the components shown in FIG. 9.
Figure 11:
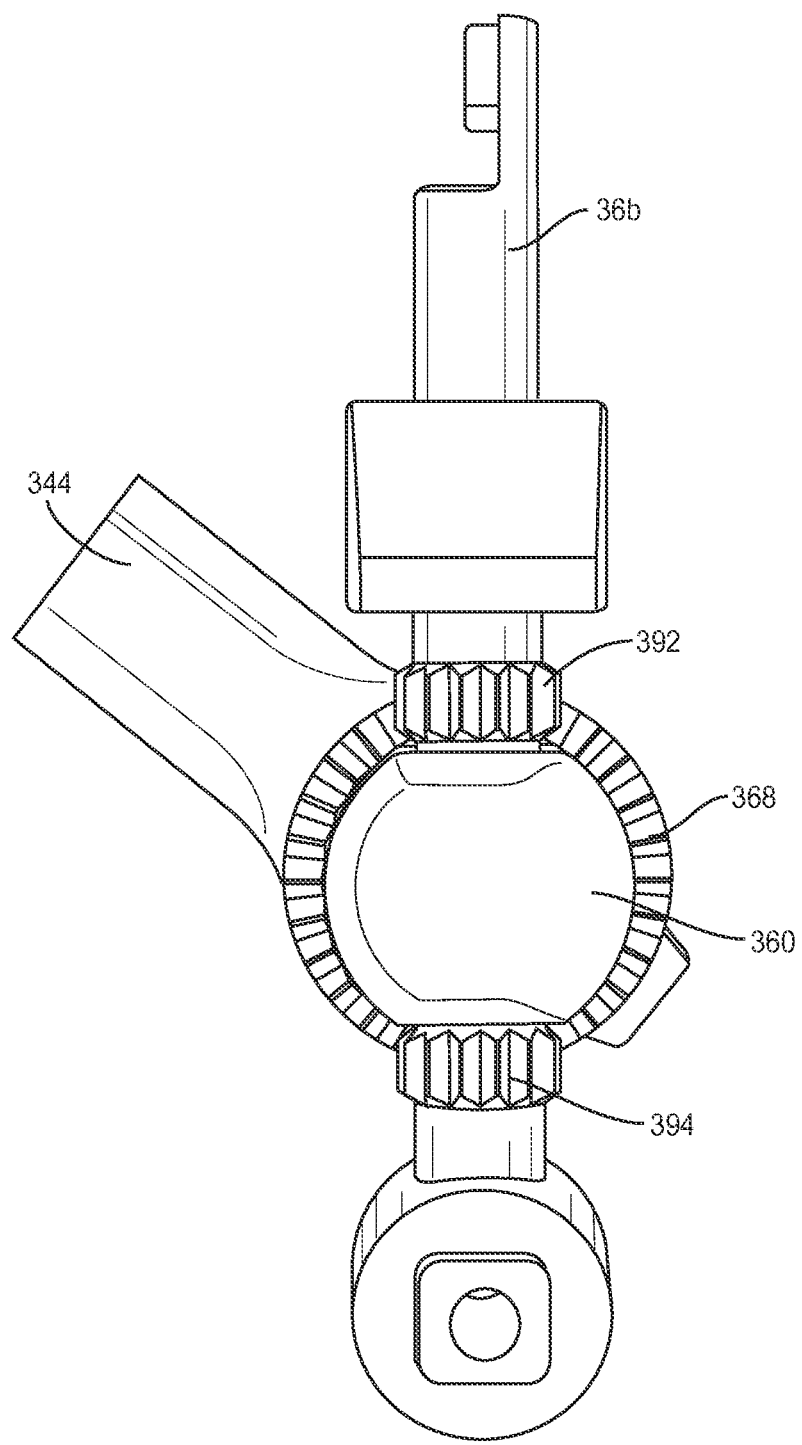
FIG. 11 is a plan view of the components shown in FIG. 9.

In one embodiment, as shown in FIGS. 9-11, surgical system 10, similar to the systems and methods described herein, includes an adaptor 340, similar to adaptors 40, 240 described herein, and comprises retractor 12 with retractor arm 14 including extension 16, and blade 30, as described herein.

Adaptor 340 is configured to connect surgical retractor 12 with retractor blade 30 for relative movement therebetween. Adaptor 340 attaches surgical retractor 12 with retractor blade 30 such that retractor blade 30 is movable in a plurality of degrees of freedom to one or a plurality of orientations, relative to axis X1 and/or extension 16, stationary surgical equipment and/or subject body B in connection with a surgical procedure, as described herein. In some embodiments, adaptor 340 is independently and selectively moveable relative to axis X1 and/or extension 16 to facilitate positioning of adaptor 340 and/or blade 30, as described herein.

Adaptor 340 includes a collar 342. Collar 342 includes an extension 344 having a surface 346. Surface 346 defines an opening 348 configured for disposal of extension 16. Extension 344 defines an axis X7. In some embodiments, surface 346 and a surface of extension 16 comprise a spheroidal joint, similar to that described herein to facilitate relative movement of adaptor 340 and extension 16. Collar 342 includes a surface 350 that defines an opening 352. Opening 352 is configured for disposal of a handle 354. Handle 354 includes a knob 356 and a shaft (not shown), similar to shaft 58, which defines an axis X9. Knob 356 includes a surface 362 that defines a socket 358. In some embodiments, socket 358 includes a hexalobe geometry configured for disposal of a similarly shaped bit of a tool, such as, for example, a driver (not shown) to engage knob 356 to rotate the shaft, as described herein. The shaft includes a threaded surface (not shown) disposed in a threaded engagement with a member, such as, for example, a jaw 360, similar to jaws 66, 260, such that jaw 360 is translatable relative to the shaft.

Collar 342 includes an inner surface 362 that defines a cavity 364 configured for disposal of jaw 360, as described herein. Collar 342 includes a surface 366 that includes a radially splined surface 368. Surface 368 is configured to engage a spaced apart gear surface of arm 36b to facilitate incremental and selective positioning of blade 30 relative to arm 14.

Jaw 360 includes an inner surface that defines a threaded passageway (not shown). The passageway is configured for disposal and threaded fixation with the shaft. In some embodiments, jaw 360 is engageable with handle 354 in threaded fixation to dispose blade 30 with retractor arm 14 between a non-locked configuration, a provisionally locked configuration and a final locked configuration, similar to that described herein. The shaft is engaged with jaw 360 to define an axis X8.

Jaw 360 includes a surface 376 that defines a cavity, such as, for example, a lateral passageway 378. Passageway 378 is configured for disposal of arm 36b, which defines an axis X8. Surface 376 includes a retaining flange 380. Flange 380 defines a recess 382 with surface 376 configured for disposal of arm 36b. In some embodiments, flange 380 is oriented in a snap fit configuration to retain arm 36b with adaptor 340. In some embodiments, adaptor 340 includes a spring (not shown) disposed within cavity 364 to bias adaptor 340 in a provisionally closed or locked configuration with arm 36b to retain arm 36b with adaptor 340 prior to fixation of retractor arm 14 in a final locked configuration. In some embodiments, the provisionally closed or locked configuration includes jaw 360 being biased and/or drawn upwardly with arm 36b relative to cavity 364. In some embodiments, the spring (not shown) is disposed about the shaft. In some embodiments, the spring (not shown) is disposed between jaw 360 and surface 362.

Arm 36b includes a surface 390 having a gear surface 392 and a gear surface 394. Surfaces 392, 394 are circumferentially disposed about surface 390 and in spaced apart relation. Surfaces 392, 394 are spaced apart for disposal with collar 342 and alignment of gear surfaces 392, 394 with spline surface 368. Surface 390 includes a smooth or even surface 396 between surfaces 392, 394. In some embodiments, surfaces 392, 394 are disposed in parallel. In some embodiments, surfaces 392, 394 are disposed in various relative orientations, such as, for example, offset, staggered, transverse, perpendicular and/or angular such as obtuse or acute.

Surfaces 392, 394 are configured for engagement with surface 368 of arm 36b to facilitate incremental and selective positioning of blade 30 relative to arm 14. Surface 368 and surfaces 392, 394 form a gear interface between collar 342 and arm 36b. In some embodiments, the gear interface facilitates locking of arm 36b with adaptor 340 at angular increments providing for a higher shear strength requiring a low torque input from the threaded engagement with the shaft and jaw 360. In some embodiments, the low torque allows for a practitioner to hand tighten adaptor 340.

Adaptor 340 is fixed with extension 16. Arm 36b is disposed with passageway 378. In some embodiments, adaptor 340 connects retractor arm 14 with retractor blade 30 such that retractor blade 30 is movable to a plurality of degrees of freedom. In some embodiments, adaptor 340 is spring pre-loaded to bias handle 354 and/or jaw 360 to a provisionally closed or locked configuration with arm 36b to retain arm 36b with adaptor 340 prior to fixation of retractor arm 14 in a final locked configuration. In some embodiments, adaptor 340 connects retractor arm 14 with retractor blade 30 to dispose retractor arm 14 and retractor blade 30 in a non-locked configuration, a provisionally locked configuration and/or a final locked configuration, as described herein.

Adaptor 340 is configured for attaching retractor arm 14 with retractor blade 30. Adaptor 340 connects retractor arm 14 with retractor blade 30 and facilitates relative movement of arm 36b and extension 16. In some embodiments, adaptor 340 connects retractor arm 14 with retractor blade 30 such that retractor blade 30 is movable in one or a plurality of degrees of freedom to one or a plurality of orientations relative to rail 18, stationary surgical equipment and/or subject body B in connection with a surgical procedure. In some embodiments, adaptor 340 connects retractor arm 14 with retractor blade 30 such that retractor blade 30 is movable in a plurality of degrees of freedom including two degrees of freedom in rotation relative to extension 16. In some embodiments, adaptor 340 connects retractor arm 14 with retractor blade 30 such that retractor blade 30 is independently and selectively moveable relative to retractor arm 14 to facilitate positioning of retractor blade 30, as described herein.

In some embodiments, retractor blade 30 is disposed in a non-locked configuration and movable in two additional degrees of freedom as facilitated by adaptor 240 including two degrees of freedom in rotation relative to extension 16. Arm 36b is rotatable relative to and about axis X9, in the direction shown by arrows H in FIG. 9, and rotatable relative to and about axis X8, in the direction shown by arrows I in FIG. 9, to one or more selected orientations relative to extension 16. In some embodiments, retractor blade 30 is disposed in a provisionally locked configuration and movable, as described herein, for selective and/or incremental adjustment of position and orientation of retractor blade 30 relative to retractor arm 14. Upon positioning of retractor blade 30 relative to extension 16 in a selected orientation, as described herein, a driver is engaged with socket 358 and/or handle 354 is manipulated to rotate the shaft in threaded engagement with jaw 360. The shaft engages arm 36b to lock blade 30 in final locked configuration with extension 16.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical adaptor comprising:
   a first member including a surface defining an opening, the opening having a projection of a first surgical instrument positioned therein, the projection defining an axis;
   a second member comprising a first end positioned in a cavity of the first member and an opposite second end defining a recess, the second end being fixed relative to the first end, the first end comprising an inner surface defining a hole having a first thread form, a second surgical instrument being received within the recess such that the second surgical instrument is movable in at least two degrees of freedom relative to the axis; and
   an actuator comprising a shaft, an outer surface of the shaft comprising a second thread form that mates with the first thread form to translate the actuator relative to the second member, the actuator being rotatable relative to the second member to move the actuator between a first orientation in which an end surface of the shaft is spaced apart from the second surgical instrument and a second orientation in which the end surface of the shaft directly engages the second surgical instrument.

2. A surgical adaptor as recited in claim 1, wherein the degrees of freedom include rotation in a first direction relative to the axis.

3. A surgical adaptor as recited in claim 2, wherein the first surgical instrument includes a retractor arm.

4. A surgical adaptor as recited in claim 1, wherein the degrees of freedom include translation along the axis.

5. A surgical adaptor as recited in claim 1, wherein the degrees of freedom include rotation in a first direction relative to the axis and rotation in a second direction relative to the axis.

6. A surgical adaptor as recited in claim 1, wherein the degrees of freedom include translation along the axis, rotation in a first direction relative to the axis and rotation in a second direction relative to the axis.

7. A surgical adaptor as recited in claim 1, wherein the first member includes a collar.

8. A surgical adaptor as recited in claim 7, wherein the collar includes an extension having a passageway configured to receive the projection.

9. A surgical adaptor as recited in claim 1, wherein the actuator is spring biased.

10. A surgical adaptor as recited in claim 1, wherein the second end of the second member includes a jaw configured to receive the second surgical instrument.

11. A surgical adaptor as recited in claim 10, wherein the jaw includes a flange to releasably retain the second surgical instrument.

12. A surgical adaptor as recited in claim 1, wherein the second surgical instrument includes a retractor blade.

13. A surgical adaptor as recited in claim 1, wherein the actuator comprises a handle that is coupled to the shaft, the handle comprising a socket that is coaxial with the shaft, a lateral cross-section of the socket including a hexalobe geometry.

14. A surgical adaptor as recited in claim 1, wherein the cavity is spaced apart from the opening.

15. A surgical adaptor as recited in claim 1, wherein the second end comprises a retaining flange that defines a portion of the recess.

16. A surgical adaptor as recited in claim 1, wherein the actuator comprises a handle that is coupled to the shaft, the handle comprising a flange that directly engages a surface of the first member when the end surface of the shaft directly engages the second surgical instrument.

17. A surgical adaptor comprising:
   a collar including an extension having a surface defining an opening, the opening having a projection of a retractor positioned therein, the projection defining an axis;
   a jaw having a first end positioned in a cavity of the collar, the jaw having a second end defining a recess, the second end being fixed relative to the first end, the first end comprising an inner surface defining a hole having a first thread form, an arm of the retractor being received within the recess such that a blade of the retractor that is coupled to the arm is rotatable in a first direction relative to the axis, rotatable in a second direction relative to the axis and translatable along the axis; and
   an actuator comprising a shaft, an outer surface of the shaft comprising a second thread form that mates with the first thread form to translate the actuator relative to the jaw, the actuator being rotatable relative to the jaw to move the actuator between a first orientation in which an end surface of the shaft is spaced apart from the arm and a second orientation in which the end surface of the shaft directly engages the arm.

18. A surgical system comprising:
   a surgical retractor having a projection that defines an axis; and
   an adaptor including a first member having an extension attachable to the surgical retractor along the axis, the adaptor further including a second member having a first end positioned in a cavity of the first member, the second member having a second end defining a recess, the second end being fixed relative to the first end, the first end comprising an inner surface defining a hole having a first thread form, an arm of the retractor being received within the recess such that a blade of the retractor that is coupled to the arm is movable in at least two degrees of freedom relative to the axis, the adaptor comprising an actuator having a shaft, an outer surface of the shaft comprising a second thread form that mates with the first thread form to translate the actuator relative to the second member, the actuator being rotatable relative to the second member to move the actuator between a first orientation in which an end surface of the shaft is spaced apart from the arm and a second orientation in which the end surface of the shaft directly engages the arm.

19. A surgical system as recited in claim 18, wherein the degrees of freedom include rotation in a first direction relative to the axis and rotation in a second direction relative to the axis.

20. A surgical system as recited in claim 18, wherein the degrees of freedom include translation along the axis, rotation in a first direction relative to the axis and rotation in a second direction relative to the axis.

* * * * *